United States Patent [19]
Lee et al.

[11] Patent Number: 6,008,292
[45] Date of Patent: Dec. 28, 1999

[54] METHOD FOR INHIBITING CALCIFICATION OF ALDEHYDE-FIXED BIOPROSTHETIC MATERIALS

[75] Inventors: Catherine Ting Lee, Laguna Hills; Jun Yang, Dove Canyon; Tan Thanh Dinh, Fountain Valley; Ernest H. Pfadenhauer, Costa Mesa, all of Calif.

[73] Assignee: Baxter International Inc., Deerfield, Ill.

[21] Appl. No.: 08/982,846

[22] Filed: Dec. 2, 1997

[51] Int. Cl.⁶ ..................................................... A61L 27/00
[52] U.S. Cl. ............................... 525/54.1; 8/94.11; 623/11
[58] Field of Search ................................ 8/94.11; 623/11; 525/54.1

[56] References Cited

U.S. PATENT DOCUMENTS

| | | | |
|---|---|---|---|
| 4,120,649 | 10/1978 | Schechter | 8/94.11 |
| 4,405,327 | 9/1983 | Pollock | 8/94.11 |
| 4,648,881 | 3/1987 | Carpentier et al. | 623/11 |
| 4,885,005 | 12/1989 | Nashef et al. | 8/94.11 |
| 4,976,733 | 12/1990 | Girardot | 623/11 |
| 5,002,566 | 3/1991 | Carpentier et al. | 623/2 |
| 5,549,666 | 8/1996 | Hata et al. | 623/2 |

FOREIGN PATENT DOCUMENTS

| | | |
|---|---|---|
| EP 0306256 | 3/1989 | European Pat. Off. |
| WO 92/14419 | 9/1992 | WIPO |
| WO 94/17841 | 8/1994 | WIPO |
| WO 96/13227 | 5/1996 | WIPO |

OTHER PUBLICATIONS

Chachra et al., "Effect of Applied Uniaxial Stress on Rate and Mechanical Effects of Cross–Linking in Tissue–Derived Biomaterials, " *Biomaterials*vol. 17, Oct 1996, 1865–1875.

Zhou et al., "Porcine Aortic Wall Flexibility Fresh vs Denacol Fixed vs Glutaraldehyde Fixed," ASIAO Journal, vol. 43, No. 5, 470–475, Sep 1997, Edwards CVS Division, Baxter Healthcare Corporation.

*Primary Examiner*—Nathan M. Nutter
*Attorney, Agent, or Firm*—Guy L. Cumberbatch; Robert D. Buyan

[57] ABSTRACT

A method for preparing collagenous biological tissues for use as implantable bioprosthetic material, and articles prepared thereby. The method generally comprises the steps of a) contacting the tissue with an aldehyde fixative to effect cross-linking of the connective tissue protein(s) and subsequently b) contacting the tissue with a polyglycidyl ether. The treatment of the crosslinked tissue with the polyglycidyl ether serves to mitigate the tissue's propensity to undergo calcification following implantation in the body.

15 Claims, No Drawings

METHOD FOR INHIBITING CALCIFICATION OF ALDEHYDE-FIXED BIOPROSTHETIC MATERIALS

FIELD OF THE INVENTION

The invention pertains generally to medical method/devices and more particularly to a method for chemically modifying glutaraldehyde-fixed bioprosthetic materials to mitigate their propensity for post-implantation calcification.

BACKGROUND OF THE INVENTION

In modern medical practice, numerous implantable devices or prostheses are formed wholly or partially of biological tissue which has been chemically "fixed" or preserved. The technique used for chemical fixation of biological tissues typically requires exposure of the biological tissue to one or more chemical agents which are capable of forming cross-linkages between connective tissue protein molecules present in the tissue.

Examples of fixed biological tissues which have been used as bioprostheses include cardiac valves, blood vessels, skin, dura mater, pericardium, ligaments and tendons. These tissues typically contain a matrix of connective tissue proteins which act as the supportive framework of the tissue.

Collagen and elastin are two connective tissue proteins which make up the connective tissue framework of most biological tissues. The pliability or rigidity of each biological tissue is largely determined by its relative amounts of collagen and elastin and/or by the physical structure and confirmation of its connective tissue frame work.

Each collagen molecule is made up of three (3) polypeptide chains intertwined in a coiled helical confirmation. The chemical fixatives (i.e., tanning agents) which are used to preserve biological tissues generally form chemical cross-linkages between the polypeptide chains within a given collagen molecule (i.e., intramolecular crosslinkages), or between adjacent collagen molecules (i.e., intermolecular crosslinkages).

Examples of chemical fixative agents which have been utilized to crosslink collagenous biological tissues include; formaldehyde, glutaraldehyde, dialdehyde starch, hexamethylene diisocyanate and certain polyepoxy compounds. Of the various chemical fixatives available, glutaraldehyde is the most widely used. Glutaraldehyde is used as the fixative for many commercially available bioprosthetic products, such as porcine bioprosthetic heart valves (i.e., the Carpentier-Edwards® stented porcine bioprosthesis; Baxter Healthcare Corporation; Edwards CVS Division, Irvine, Calif. 92714-5686), bovine pericardial heart valve prostheses (e.g., Carpentier-Edwards® Pericardial Bioprosthesis, Baxter Healthcare Corporation, Edwards CVS Division; Irvine, Calif. 92714-5686) and stentless porcine aortic prostheses (e.g., Edwards® PRIMA™ Stentless Aortic Bioprosthesis, Baxter Edwards AG, Spierstrasse 5, GH6048, Horn, Switzerland).

One problem associated with the implantation of bioprosthetic materials is that the connective tissue proteins within these materials tend to undergo calcification. Such calcification can result in undesirable stiffening or degradation of the bioprosthesis. Both intrinsic and extrinsic calcification are known to occur in fixed collagenous bioprostheses, although the exact mechanism(s) by which such calcification occurs is unknown.

Clinical experience and experimental data has taught that glutaraldehyde-fixed collagenous bioprostheses may tend to calcify sooner than bioprostheses which have been fixed by other nonaldehyde fixative agents. Such accelerated calcification of glutaraldehyde-fixed bioprostheses has been reported to predominantly occur in pediatric patients. (Carpentier et al., Continuing Improvements in Valvular Bioprostheses, J. Thoracic Cardiovasc. Surg. 83:27–42, 1982.) Such accelerated calcification is undesirable in that it may lead to deterioration and/or failure of the implanted bioprostheses. In view of this propensity for accelerated calcification of glutaraldehyde-fixed bioprostheses in young patients, surgeons typically opt to implant mechanical heart valves or homografts (if available) into pediatric or relatively young patients (i.e., patients under 65 years of age), rather than glutaraldehyde-fixed bioprosthetic valves. However, patients who receive mechanical valve implants require ongoing treatment with anticoagulant medications, which can be associated with increased risk of hemorrhage. Also, homografts are of limited availability and may carry pathogens which can result in infection.

The factors which determine the rate at which glutaraldehyde-fixed bioprosthetic grafts undergo calcification have not been fully elucidated. However, factors which are thought to influence the rate of calcification include:

a) patient's age;
b) existing metabolic disorders (i.e., hypercalcemia, diabetes, etc.);
c) dietary factors;
d) race;
e) infection;
f) parenteral calcium administration;
g) dehydration;
h) distortion/mechanical factors;
i) inadequate coagulation therapy during initial period following surgical implantation; and
j) host tissue responses.

Many investigators have attempted to discover ways of mitigating the in situ calcification of glutaraldehyde-fixed bioprostheses. Included among these calcification mitigating techniques are the methods described in U.S. Pat. No. 4,885,005 (Nashef et al.) entitled Surfactant Treatment of Implantable Biological Tissue To Inhibit Calcification; U.S. Pat. No. 4,648,881 (Carpentier et al.) entitled Implantable Biological Tissue and Process For Preparation Thereof; U.S. Pat. No. 4,976,733 (Girardot) entitled Prevention of Prosthesis Calcification; U.S. Pat. No. 4,120,649 (Schechter) entitled Transplants; U.S. Pat. No. 5,002,2566 (Carpentier) entitled Calcification Mitigation of Bioprosthetic Implants; EP 103947A2 (Pollock et al.) entitled Method For Inhibiting Mineralization of Natural Tissue During Implantation and WO84/01879 (Nashef et al.) entitled Surfactant Treatment of Implantable Biological Tissue to Inhibit Calcification; and, in Yi, D., Liu, W., Yang, J., Wang, B., Dong, G., and Tan, H.; *Study of Calcification Mechanism and Anti-calcification On Cardiac Bioprostheses* Pgs. 17–22, Proceedings of Chinese Tissue Valve Conference, Beijing, China, June 1995.

Because none of the previously known calcification mitigation, technique has proven to be optimal for glutaraldehyde-fixed tissues. There exists a need in the art for the development of new methods for inhibiting or mitigating calcification of glutaraldehyde-fixed biological tissues.

SUMMARY OF THE INVENTION

Broadly stated, the present invention provides methods for improving the biocompatability and/or performance of glutaraldehyde-fixed biological tissue by treating the tissue with a polyglycidyl ether concurrently with or following the glutaraldehyde fixation.

In many applications, the method of the present invention will be carried out by the following steps:

a. preparing a biological tissue which contains connective tissue proteins;

b. contacting the biological tissue with an aldehyde fixative (e.g., formaldehyde or glutaraldehyde) to effect crosslinking of the connective tissue proteins within the tissue; and c. concurrently with, or after, the completion of step (b), contacting the tissue with a polyglycidyl ether.

In accordance with the above-summarized method of the present invention, steps b and c may be carried out using separate aldehyde and polyglycidyl ether solutions—or by using an aldehyde/polyglycidyl admixture. For example, the tissue may be initially contacted with the aldehyde to carry out step b completion and thereafter the tissue may be removed from the aldehyde fixative and subsequently contacted with the polyglycidyl ether. Alternatively, the tissue be initially contacted with the aldehyde for an initial period of time to permit partial or complete crosslinking of the connective tissue protein(s) and, thereafter, the polyglycidyl ether(s) may be added to the aldehyde—to form a polyglycedyl ether/aldehyde admixture in the presence of the fully or partially crosslinked tissue. Alternatively, a polyglycidyl ether/aldehyde admixture may be initially prepared and the fresh tissue may then be contacted with such admixture to carry out steps b (cross-linking) and c (post-crosslinking ether treatment) using a single admixture.

Further in accordance with the present invention, there are provided various types of bioprosthetic articles which are wholly or partially formed of tissue which has been prepared by the above-summarized method of the present invention. Examples of the types of biological tissues which may be utilized to prepare bioprosthetic articles in accordance with this invention include, but are not necessarily limited to: heart valves, venous valves; blood vessel; ureter; tendon; dura mater; skin; pericardium; cartilage (e.g., meniscus); ligament; bone; intestine (e.g., intestinal wall); and periostium.

Further aspects and objects of the present invention will become apparent to those skilled in the relevant art, upon reading and understanding the detailed description of presently preferred embodiments set forth below.

DETAILED DESCRIPTION OF THE PREFERRED EMBODIMENTS

The following detailed description and the accompanying drawing to which it refers are provided for purpose of describing and illustrated presently preferred embodiments of the invention only, and are not intended to limit the scope of the invention in any way.

With reference of the flow diagram of FIG. 1, a presently preferred method for preparing a fixed biological material in accordance with the present invention comprises the steps of:

(a) preparing a biological tissue which contains connective tissue proteins;

(b) contacting the biological tissue with an aldehyde fixative, such as glutaraldehyde, to effect crosslinking of the connective tissue proteins within the tissue; and (c) concurrently with or after the completion of step (b), contacting the tissue with a polyglycidyl ether.

In performing this method of the present invention, steps b and c may be carried out using separate aldehyde and polyglycidyl ether solutions—or by using an aldehyde/polyglycidyl admixture. For example, the tissue may be initially contacted with the aldehyde to carry out step b completion and thereafter the tissue may be removed from the aldehyde fixative and subsequently contacted with the polyglycidyl ether. Alternatively, the tissue be initially contacted with the aldehyde for an initial period of time to permit partial or complete crosslinking of the connective tissue protein(s) and, thereafter, the polyglycidyl ether(s) may be added to the aldehyde—to form a polyglycidyl ether/aldehyde admixture in the presence of the fully or partially crosslinked tissue. Alternatively, a polyglycidyl ether/aldehyde admixture may be initially prepared and the fresh tissue may then be contacted with such admixture to carry out steps b (cross-linking) and c (post-crosslinking ether treatment) using a single admixture.

The preferred fixative solution for step b of the method is 0.625% glutaraldehyde buffered to a pH of approximately 7.4 by a suitable buffer such as a phosphate buffer.

The preferred polyglycidyl ethers for step c of the method are ethylene glycol diglycidyl ether (Denacol EX810, Nagese Chemical Co., Osaka, Japan) and glycerol polyglycidyl ether (Denacol EX313, Nagese Chemical Co., Osaka, Japan). Step c may be carried out by immersing the tissue in a solution containing between 1 and 10 percent by volume of the polyglycidyl ether. Additionally, the polyglycidyl ether solution used in Step c may contain one or more alcohol(s), such as ethanol, preferably at an ethanol concentration of approximately 10–30 percent by volume.

EXAMPLE 1

Post-Glutaraldehyde Fixation Treatment with Ethylene Glycol Diglycidyl Ether PROCEDURE: Bovine pericardial tissue is fixed with glutaraldehyde by a 14 day treatment with a 0.625% solution in pH 7.4 phosphate buffer. After washing three times in water, the tissue is treated with a solution of 2% Denacol EX-810 and 20% ethanol in water for 120 hours at 43–46° C. As a control, glutaraldehyde fixed tissue is treated with the sterilizing solution of Glutaraldehyde (0.625% in pH 7.4 phosphate), ethanol (20%) and Tween 80 (0.2%) for 24–28 hours at 43–46° C. Tissues are stored in the final solution at room temperatures until use.

Calcification potential is measured by exposing the tissue to solutions of:

(1) Calcium Chloride (2.5 mM in pH 7.0 Tricine buffer) or (2) Human Serum

For each condition, 3×1 cm$^2$ pieces of fixed tissue are added to 50 ml of treatment solution and incubated at 37° C. in an orbital shaker for three weeks. One piece of tissue is removed every week for elemental analysis. The tissue is washed 4 times with water for 40 minutes each time, lyophilized, weighed, then digested with 4 ml of 70% nitric acid at 100° C. Samples are then analyzed for elemental Calcium.

RESULTS: Calcium content, expressed at % of total weight of the tissue, is summarized in the table below.

| Condition | | 1 week (Ca %) | 2 weeks (Ca %) | 3 weeks (Ca %) |
| --- | --- | --- | --- | --- |
| Ca₂Cl | Control | 0.18% | 0.15 | 0.22 |
|  | Denacol EX 810 | 0.02% | 0.08 | 0.06 |
| serum | control | 0.01 | 0.44 | 1.26 |
|  | Denacol EX 810 | 0.00 | 0.11 | 0.62 |

This experiment demonstrates that ethylene glycol diglycidyl ethers have the ability to mitigate tissue calcification after glutaraldehyde fixation.

One possible mechanism by which the polyglycidyl ether treatment serves to mitigate calcification of glutaraldehyde fixed tissue may be through a direct reaction between the glutaraldehyde crosslinkages (or free glutaraldehyde which remains present in the tissue) and the polyglycidyl ether.

EXAMPLE 2

Reaction of Polyglycidyl Ethers with Glutaraldehyde

PROCEDURE: Solutions of both 4% ethylene glycol diglycidyl ether (Denacol EX 810) and 4% glycerol polyglycidyl ether (Denacol EX 313) are mixed with 0.625% glutaraldehyde in an aqueous solution buffered with phosphate to pH 7.4. The reaction is allowed to proceed at room temperature for 7 days. The reaction mixture, along with controls of each component alone or in buffer, and freshly made controls of each component, are analyzed by ultraviolet (UV)-Visible spectroscopy and reactivity to N-a-acetyl-lysine on days 1, 2, 3 and 7, and thin layer chromatography on day 7.

RESULT: UV spectra of the reaction solution shows changes over time at 235 nm. This wavelength has previously been shown to be characteristic of a homopolymer of glutaraldehyde, but in this case is probably due to the formation of a copolymer of polyglycidyl ether and glutaraldehyde. The table below shows the 235 nm absorbence from day 0 to day 7. Dilutions are made where necessary to bring absorbence readings within the spectrometer dynamic range.

| | Absorbence at 235 nm | | | | |
| --- | --- | --- | --- | --- | --- |
| Solution | Day 0 | Day 1 | Day 2 | Day 3 | Day 7 |
| GA | 2.1 | 2.4 | 2.7 | 2.9 | 3.0 |
| EX313 | 0.37 | 0.32 | 0.35 | 0.35 | 0.32 |
| EX810 | 0.12 | 0.16 | 0.17 | 0.17 | 0.16 |
| GA + EX313 | 2.5 | 13.6 | 17.2 | 21.0 | 24.8 |
| GA + EX810 | 2.3 | 15.6 | 18.3 | 22.0 | 25.3 |

Reactivity of glutaraldehyde is measured by its ability to form a complex with N-a-acetyl-lysine, which has a strong absorption at 265 nm. At each time point, an aliquot of each solution is removed, diluted 1:10, and 1.0 ml added to 0.5 ml of 15 mM N-a-acetyl-lysine in pH 7.4 phosphate buffer. After 45 min., the reaction is further diluted 4:1, and read at 265 nm. Reactivity is compared to equally aged glutaraldehyde mixed with freshly made Denacol. The table below shows the % glutaraldehyde reactivity lost, as measured by a decrease in 265 absorbence, relative to that of a fresh Denacol solution.

| | % Activity Lost | | | |
| --- | --- | --- | --- | --- |
| Solution | Day 1 | Day 2 | Day 3 | Day 7 |
| GA + EX313 | 23 | 44 | 50 | 66 |
| GA + EX810 | 41 | 54 | 61 | 75 |

Reaction products are detected by a thin-layer chromatography (TLC) system, consisting of Whatman K6 silica plates developed with chloroform:methanol (95:5). Visualization was accomplished by exposure to Iodine vapor. Glutaraldehyde and Denacol each show characteristic components after visualization, however the reaction mix at 7 days shows a dark residue at the origin, indicating a new reaction product and consistent with copolymer formation.

The invention has been described above with reference to certain presently preferred embodiments or examples only and no attempt has been made to exhaustively describe all possible embodiments or examples of the invention. Those skilled in the art will recognize that various modifications, additions and changes may be made to the particular embodiments and examples described above without departing from the intended spirit and scope of the invention. Accordingly, it is intended that all such modifications, additions and changes be included within the scope of the following claims.

What is claimed is:

1. A method for mitigating calcification of a collagenous bioprosthetic material which has previously been crosslinked with an aldehyde corsslinking agent, said method comprising the step of:
    a. after the collagenous bioprosthetic material has been crosslinked by the aldehyde crosslinking agent, contacting the crosslinked collagenous bioprosthetic material with a polyglycidyl ether.

2. The method of claim 1 wherein the polyglycidyl ether used in Step a is selected from the group of polyglycidyl ethers consisting of:
    ethylene glycol diglycidyl ether; and
    glycerol polyglycidyl ether.

3. The method of claim 1 wherein Step a comprises:
    contacting the bioprosthetic material with a solution containing approximately 1–10 percent by volume of at least one polyglycidyl ether.

4. The method of claim 1 wherein Step a comprises:
    contacting the bioprosthetic material with a solution containing approximately 1–10 percent by volume ethylene glycol diglycidyl ether.

5. The method of claim 1 wherein Step a comprises:
    contacting the bioprosthetic material with a solution containing approximately 1–10 percent by volume glycerol polyglycidyl ether.

6. The method of claim 1 wherein Step a comprises:
    contacting the bioprosthetic material with a solution containing approximately 1–10 percent by volume ethylene glycol diglycidyl ether in combination with approximately 10–30 percent by volume ethanol.

7. The method of claim 4 wherein Step a comprises:
    contacting the bioprosthetic material with a solution containing approximately 1–10 percent by volume glycerol polyglycidyl ether in combination with approximately 10–30 percent by volume ethanol.

8. The method of claim 1 wherein step a comprises:
    contacting the bioprosthetic material with a mixture containing at least two polyglycidyl ethers.

9. The method of claim 8 wherein step a comprises:
contacting the bioprosthetic material with a mixture of ethylene glycol diglycidyl ether and glycerol polyglycidyl ether.

10. A method for preparing a fixed biological tissue which contains connective tissue protein, said method comprising the steps of:
   a. providing a biological tissue which contains at least one connective tissue protein;
   b. contacting the biological tissue with an aldehyde fixative to effect crosslinking of the connective tissue protein (s) within the tissue; and, thereafter,
   c. contacting the aldehyde-fixed biological tissue with a polyglycidyl ether.

11. The method of claim 10 wherein step (b) comprises:
contacting the biological tissue with a solution of approximately 0.625% glutaraldehyde buffered to pH 7.4 with phosphate buffer.

12. The method of claim 10 wherein steps (b) and (c) are carried out in separate containers.

13. The method of claim 10 wherein the method further comprises rinsing of the biological tissue between steps (b) and (c).

14. The method of claim 10 wherein step (b) is performed by immersing the biological tissue in a first solution containing an aldehyde fixative for a period of time sufficient to effect aldehyde crosslinking of the tissue and thereafter, step (c) is performed by adding a polyglycidyl ether to the first solution wherein the biological tissue is immersed.

15. The method of claim 10 wherein steps (b) and (c) are carried out by initially immersing the biological tissue in a an aldehyde solution and thereafter adding at least one polyglycidyl ether to the glutaraldehyde solution to form the aldehyde/polyglycidyl ether admixture.

* * * * *